United States Patent

Sato et al.

Patent Number: 4,537,874
Date of Patent: Aug. 27, 1985

[54] CATALYST FOR PRODUCTION OF UNSATURATED ALDEHYDES

[75] Inventors: Takahisa Sato; Masahiro Takata, both of Himeji; Michio Ueshima, Nishinomiya; Isao Nagai, Suita, all of Japan

[73] Assignee: Nippon Shokubai Kagaku Kogyo Co Ltd, Osaka, Japan

[21] Appl. No.: 543,150

[22] Filed: Oct. 18, 1983

[30] Foreign Application Priority Data

Oct. 22, 1982 [JP] Japan ................. 57-184668
Jul. 27, 1983 [JP] Japan ................. 58-135740

[51] Int. Cl.³ .............. B01J 23/16; B01J 21/02; B01J 27/14; B01J 23/84
[52] U.S. Cl. .................... 502/311; 502/205; 502/206; 502/212; 502/213; 502/306; 502/314; 502/316; 568/479; 562/546; 562/547
[58] Field of Search ........... 502/205, 206, 212, 213, 502/306, 311, 314, 316

[56] References Cited

U.S. PATENT DOCUMENTS

| | | | |
|---|---|---|---|
| 2,941,007 | 6/1960 | Callahan et al. | 502/212 X |
| 3,089,909 | 5/1963 | Barclay et al. | 502/310 X |
| 3,171,859 | 3/1965 | Sennewald et al. | 502/212 X |
| 3,522,299 | 7/1980 | Takenaka et al. | 502/212 X |
| 3,803,204 | 4/1974 | Grasselli et al. | 502/205 X |
| 3,825,600 | 7/1974 | Ohara et al. | 502/243 X |
| 4,052,450 | 10/1977 | Krabetz et al. | 502/314 X |
| 4,148,757 | 4/1979 | Brazdil et al. | 502/210 X |
| 4,155,938 | 5/1979 | Yamamoto et al. | 502/205 X |
| 4,162,234 | 7/1979 | Grasselli et al. | 502/205 |
| 4,167,494 | 9/1979 | Grasselli et al. | 502/206 X |
| 4,280,928 | 7/1981 | Kirch et al. | 502/205 |
| 4,424,141 | 1/1984 | Grasselli et al. | 502/205 |
| 4,438,217 | 3/1984 | Takata et al. | 502/205 |

Primary Examiner—D. E. Gantz
Assistant Examiner—William G. Wright
Attorney, Agent, or Firm—Sherman & Shalloway

[57] ABSTRACT

A catalyst for the production of unsaturated aldehydes is provided which is represented by the general formula $$Bi_a W_b Fe_c Mo_d A_e B_f C_g D_h O_x$$

wherein Bi represents bismuth, W represents tungsten, Fe represents iron, Mo represents molybdenum, O represents oxygen, A represents nickel and/or cobalt, B represents at least one element selected from the group consisting of alkali metals, alkaline earth metals and thallium, C represents at least one element selected from the group consisting of phosphorus, arsenic, boron, antimony, tin, cerium, lead and niobium, D presents at least one element selected from the group consisting of silicon, aluminum, zirconium and titanium, a, b, c, d, e, f, g, h and x represent the atomic ratios of the individual elements, and when d is taken as 12, $a=0.1-10.0$, $b=0.5-10.0$ (provided that $a/b=0.01-6.0$), $c=0.1-10.0$, $e=2.0-20.0$, $f=0.001-10.0$, $g=0-10.0$, and $h=0-30$, and x takes a number determined by the atomic valences of the individual elements. The Bi component is introduced thereinto in the form of an oxide obtained beforehand by calcining a mixture of a bismuth compound and a tungsten compound at a temperature of 600° to 900° C.

2 Claims, No Drawings

CATALYST FOR PRODUCTION OF UNSATURATED ALDEHYDES

This invention relates to a catalyst for producing acrolein and acrylic acid or methacrolein and methacrylic acid by the vapor phase catalytic oxidation of propylene, isobutylene or tertiary butanol with a gas containing molecular oxygen. More specifically, this invention relates to a catalyst for obtaining acrolein and acrylic acid or methacrolein and methacrylic acid, particularly acrolein or methacrolein as a main product, in high yields and high selectivities by the vapor phase catalytic oxidation of propylene, isobutylene or tertiary butanol with a gas containing molecular oxygen such as air.

Numerous proposals have been made in the past about catalysts for catalytically oxidizing olefins in the vapor phase to form the corresponding unsaturated aldehydes.

A typical example is a catalyst composed mainly of molybdenum and bismuth. For example, U.S. Pat. No. 2,941,007 discloses a catalyst composed of bismuth molybdate and bismuth phosphomolybdate; U.S. Pat. No. 3,171,859, a catalyst comprising iron, bismuth, phosphorus and molybdenum as constituent elements; and U.S. Pat. No. 3,522,299, a catalyst comprising nickel, cobalt, iron, bismuth and molybdenum as main constituent elements and phosphorus, arsenic, boron, potassium, rubidium and cesium as subsidiary constituent elements.

Some catalysts composed mainly of tungsten and bismuth or some catalysts composed mainly of molybdenum, bismuth and tungsten are also known U.S. Pat. No. 3,089,909 discloses a catalyst composed of a tungstate of bismuth, and U.S. Pat. No. 3,825,600 discloses a catalyst comprising molybdenum, cobalt, iron, bismuth, tungsten, silicon and an alkali metal as constituent elements.

Many of these catalysts which were proposed earlier proved to be unsatisfactory for industrial applications in regard to the yields of acrolein and acrylic acid or methacrolein and methacrylic acid. But some of those proposed recently have been found to be industrially feasible as a result of various improvements achieved.

Even those industrially feasible catalysts, when acutally used industrially, have not been able to give acrolein and acrylic acid or methacrolein and methacrylic acid in so high selectivities and yields as described in the working examples of patent specifications which describe these catalysts and have achieved only much lower levels of results. This is presumably because in actual industrial use, the very exothermic nature of the aforesaid catalytic vapor-phase oxidation reaction causes the occurrence of abnormally high-temperature localized areas, known in the art as hot spots, in the catalyst layer to induce excessive oxidation. Another cause would be that since the packed height of the catalyst is large and the pressure in the catalyst layer gradually changes from its inlet toward its outlet, the oxidation reaction taking place therein is remote from an ideal one. Furthermore, a multi-component catalyst comprising molybdenum as a main ingredient is difficult to obtain in uniform quality because molybdenum readily reacts with many elements to form complicated complex salts of molybdenum. Hence, the reproducibility of its performance is unsatisfactory. It is natural therefore that not all of catalysts produced should be able to show such high levels of performance as described in the working examples of the above-cited patent documents.

It is an object of this invention to provide a catalyst for producing unsaturated aldehydes comprising molybdenum, bismuth and tungsten, which is free from the aforesaid defects in industrial applications.

As a catalyst meeting this object, the present invention provides a catalyst for the production of unsaturated aldehydes, said catalyst being represented by the general formula

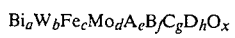

wherein Bi represents bismuth, W represents tungsten, Fe represents iron, Mo represents molybdenum, O represents oxygen, A represents nickel (Ni) and/or cobalt (Co), B represents at least one element selected from the group consisting of alkali metals, alkaline earth metals and thallium, C represents at least one element selected from the group consisting of phosphorus (P), arsenic (As), boron (B), antimony (Sb), tin (Sn), cerium (Ce), lead (Pb) and niobium (Nb), D represents at least one element selected from the group consisting of silicon (Si), aluminum (Al), zirconium (Zr) and titanium (Ti), a, b, c, d, e, f, g, h and x represent the atomic ratios of the individual elements, and when d is taken as 12, a=0-.1-10.0, preferably 0.5-5.0, b=0.5-10.0, preferably 0.5-4.0 (provided that a/b=0.01-6.0, preferably 0.1-4.0), c=0.1-10.0, preferably 0.2-5.0, e=2.0-20.0, preferably 3.0-10.0, f=0.001-10.0, preferably 0.02-2.0, g=0-10.0, preferably 0-5.0 and h=0-30, preferably 0.5-10.0, and x takes a number determined by the atomic valences of the individual elements; the Bi component being introduced thereinto in the form of an oxide obtained beforehand by calcining a mixture of a bismuth compound and a tungsten compound at a temperature of 600° to 900° C.

The catalyst of this invention is characterized by the fact that bismuth is combined very stably with tungsten, and it can maintain its high catalytic performance even in a reaction carried out for an extended period of time This stable combination between bismuth and tungsten is achieved by calcining bismuth and tungsten at temperature of as high as 600° to 900° C.

Academic works have been conducted for some time on compounds composed of bismuth and tungsten, and for example, Journal of Catalysis, vol. 31, pages 200 to 208 (1973) clarified the existence of various bismuth tungstates. Investigations of the present inventors showed that these tungstates are active in the oxidation of olefins at high temperatures exceeding 400° C., but the levels of their activities are far from being satisfactory in industrial use. On further investigations, however, the present inventors found that by combining such a bismuth tungstate further with molybdenum, iron and other metal elements, there can be obtained a catalyst which has good heat stability and superior catalytic performance at low temperatures and gives high space time yields.

U.S. Pat. No. 4,148,757 proposes a method of preparing a catalyst in which a mixture of bismuth and tungsten is added to the other catalyst ingredients. In this method, however, calcination is not performed under such conditions as will lead to the formation of a stable bismuth tungsten compound beforehand.

In contrast, the catalyst of this invention has a very high level of performance and is prepared by using bismuth and tungsten which have been calcined at high temperatures beforehand. This catalyst preparing method is very advantageous industrially since it has much better reproducibility than conventional methods for preparing catalysts composed mainly of bismuth and molybdenum compounds.

Furthermore, it is surprising to note that in the catalyst of this invention, bismuth is very firmly combined with tungsten, and X-ray diffraction analysis showed that during the preparation of the catalyst, bismuth remains firmly combined with tungsten and therefore, is prevented from forming such bismuth compounds as bismuth trioxide and bismuth molybdate. It has thus been shown that in the catalyst of this invention, bismuth and tungsten, while being kept firmly combined with each other, are further combined with the other constituent elements. X-ray diffraction analysis has led to the confirmation that even after the catalyst has been used in the oxidation of olefins over a long period of time, the state of combination of the constituent elements in the catalyst scarcely changes.

In addition, with the catalyst of this invention, the reaction temperature can be maintained lower than in the prior art, and the total yield of acrolein and acrylic acid or methacrolein and methacrylic acid can be increased, and the selectivity of acrolein or methacrolein can be increased.

Preferably, the catalyst of this invention is molded in a ring shape having an opening in the lengthwise direction so that it has an outside diameter of 3.0 to 10.0 mm with a length 0.5 to 2.0 times the outside diameter and an inside diameter 0.1 to 0.7 times the outside diameter. By molding the catalyst in this manner, the following advantages can be obtained.

(1) The geometrical surface area of the catalyst increases, and thereby, the conversion of an olefin increases. Acrolein or methacrolein formed in the pores of the catalyst diffuses more rapidly than in cylindrical catalysts because passages allowed for separation and diffusion are shortened. As a result, a consecutive reaction of acrolein or methacrolein to acrylic acid or merthacrylic acid, acetic acid, carbon monoxide and carbon dioxide decreases.

(2) As can naturally be anticipated from the ring-like shape, the pressure drop in the catalyst layer decreases, and in commercial production, the expenditure for power consumption of blowers can be curtailed.

(3) The removal of heat from hot spots caused by the very exothermic nature of the catalytic vapor-phase oxidation is increased, and the aforesaid exothermic consecutive reaction is decreased. Accordingly, the temperature of the hot spots decreases, and the rise in pressure drop caused by the sublimation of molybdenum as one catalyst ingredient during the reaction is reduced. This results in an increase in the active lifetime of the catalyst.

Variou methods of preparing the catalyst of this invention may be chosen as desired so long as the aforesaid characteristic features can be retained.

One preferred method of preparing the bismuth-tungsten combined product is shown below.

A bismuth compound such as bismuth nitrate, bismuth hydroxide or bismuth oxide and a tungsten compound such as ammonium paratungstate or tungsten oxide are mixed together with a small amount of water. The mixture is dried, and then calcined at high temperatures of 600° to 900° C., preferably 700° to 850° C. The calcined product is pulverized. The pulverization is better performed to a finer size, but pulverization to too fine a size is wasteful. Usually, sizes smaller than 100 mesh are sufficient. Thus, the bismuth-tungsten compound can be obtained.

One specific example of preparing the catalyst composition of this invention using the resulting bismuth-tungsten combined product is shown below.

An aqueous solution of an iron compound such as iron nitrate is added to an aqueous solution of a molybdenum compound such as ammonium molybdate. Furthermore, aqueous solutions of metal elements A, B, C and D are added. For example, an aqueous solution of cobaltous nitrate (when A is cobalt), an aqueous solution of an alkali metal hydroxide (when B is an alkali metal), an aqueous solution of phosphoric acid (when C is phosphorus) and colloidal silica (when D is silicon) are added, and all the ingredients added are well mixed. The pulverized bismuth-tungsten combined product is added to the resulting slurry and well mixed. The mixture is concentrated. The resulting clay-like material is molded and then calcined in the air at a temperature of 350° to 650° C., preferably 400° to 600° C. to obtain a finished catalyst.

As required, a powdery carrier material may be added to the aforesaid slurry. The carrier is selected, for example, from silica gel, alumina, silicon carbide, diatomaceous earth, titanium oxide, Celite (trademark), etc. Silica gel, titanium oxide and Celite are especially suitable.

In the bismuth-tungsten combined product, i.e. the oxide formed from a bismuth and a tungsten compound, the atomic ratio of bismuth to tungsten is from 0.01 to 6.0, preferably from 0.1 to 4.0. If this atomic ratio exceeds 6.0, the bismuth-tungsten combined product cannot assume a stable state of combination, and during preparation or use of the catalyst, the combination of bismuth with tungsten is destroyed, and bismuth recombines with the other ingredients. Consequently, the combination of the catalyst ingredients gets out of balance, and the results obtained tend to be objectionable.

The bismuth-tungsten combined product must be one which is obtained by calcining a bismuth compound and a tungsten compound at a temperature in the range of 600° to 900° C. By calcination at such a high temperature, a stable oxide is formed. Incorporating this oxide into the catalyst of this invention increases its catalytic performance to a very high level. A product obtained by calcining a bismuth compound and a tungsten compound at a temperature lower than 600° C. is not stable in the catalyst even if the bismuth/tungsten atomic ratio satisfies the aforesaid range. Such a product may destroy the balance of combination during preparation or use of the catalyst. A product obtained by calcining a bismuth compound and a tungsten compound at a temperature exceeding 900° C. is, in most cases, not a stable combined product and is susceptible to change in the catalyst.

The raw materials for the catalyst of this invention are not limited to the above-exemplified compounds. For example, in the case of bismuth and tungsten components, bismuth halides (such as bismuth chloride), bismuth carbonate, bismuth bicarbonate, bismuth hydroxide, organic acid salts of bismuth (such as bismuth acetate), alkali metal tungstates (such as sodium tungstate), and tungsten halides (such as tungsten chloride) may also be used. Needless to say, when halides or alkali metal salts are used, the slurry need to be fully washed after filtration. With regard to the other catalyst components such as molybdenum and iron, not only their nitrates and organic acid salts but also any other compounds thereof which can form various oxides under the catalyst preparing conditions may be used. Compounds containing two or three constituent elements of the catalyst may of course be used equally.

Any other catalyst preparing methods can be used by which the catalyst ingredients are present in a uniform mixture. For example, the desired catalyst can be obtained by mixing the bismuth-tungsten compound in powder form with a powdery mixture of the oxides of cobalt, iron, molybdenum, silicon and alkali metal oxide, adding a binder such as carboxymethyl cellulose which becomes extinct upon calcination, kneading them uniformly, and working up the resulting kneaded mixture in the manner described hereinabove.

When a starting gaseous mixture composed of 1 to 12% by volume of an olefin or tertiary butanol, 3 to 20% by volume of oxygen, 0 to 60% by volume of steam and 20 to 80% by volume of an inert gas such as nitrogen gas or carbon dioxide gas is reacted in the presence of the catalyst obtained as above at a reaction temperature of 250° to 450° C. and a pressure of 1 to 10 atmospheres for a contact time of 1.0 to 10.0 seconds, the corresponding unsaturated aldehyde can be produced.

The catalyst of this invention can be used either in a fixed bed-type reaction or in a fluidized bed-type reaction.

The following Examples and Comparative Examples illustrate the present invention in greater detail. It should be understood that the invention is not limited to the following examples alone.

The conversions, selectivities and one-pass yields in the present invention are defined as follows:

$$\text{Conversion (\%)} = \frac{\text{Moles of the olefin or t-butanol reacted}}{\text{Moles of the olefin or t-butanol fed}} \times 100$$

$$\text{Selectivity (mole \%)} = \frac{\text{Moles of (meth)acrolein or (meth)acrylic acid formed}}{\text{Moles of the olefin or t-butanol reacted}} \times 100$$

$$\text{One-pass yield (mole \%)} = \frac{\text{Moles of (meth)acrolein or (meth)acrylic acid formed}}{\text{Moles of the olefin or t-butanol}} \times 100$$

EXAMPLE 1

Bismuth nitrate (486 g) was dissolved in 1000 ml of distilled water acidified with 104 ml of concentrated nitric acid. To the resulting aqueous solution was added 1100 ml of aqueous ammonia (28%) to obtain a white precipitate. The precipitate was collected by filtration and washed with water. The resulting white cake was fully mixed with 464 g of tungsten trioxide. The mixture was dried at 230° C. for 16 hours, and then calcined at 750° C. for 2 hours under an air current. The yellow mass obtained was pulverized to a size smaller than 100 mesh to obtain a yellow powder. X-ray diffraction analysis (cathode Cu-K$_\alpha$) of the powder showed that it is a mixture of Bi$_2$(WO$_4$)$_3$ having peaks at d=2.973, 3.207, 2.706, 1.648 and 1.915 and WO$_3$ having peaks at d=3.632, 3.817, 3.739 and 2.610. The results of this analysis agree with the description of the above-cited Journal of Catalysis, vol. 31, pages 200 to 208 (1973). No peak ascribable to bismuth oxide was observed.

Separately, an aqueous solution of 1164 g of cobalt nitrate in 800 ml of distilled water, an aqueous solution of 118 g of ferric nitrate in 400 ml of distilled water, and an aqueous solution of 400 g of silica sol containing 20% by weight of silica and 5.1 g of potassium nitrate in 100 ml of distilled water were added to an aqueous solution of 1766 g of ammonium molybdate in 8000 ml of distilled water, and the mixture was stirred at room temperature.

The resulting suspension was concentrated under heat, dried and pulverized. The yellow powder obtained as above was added to this powder, and they were fully mixed. Distilled water was added, and the mixture was well kneaded. The kneaded mixture was molded into pellets having a diameter of 5.5 mm and a length of 7 mm, dried, and then calcined under an air current at 450° C. for 6 hours to form a finished catalyst. The composition by atomic ratios of this catalyst excepting oxygen was as follows (the compositions of catalysts will be expressed in this way hereinafter):

$$Bi_{1.2}W_{2.4}Fe_{0.35}Mo_{12}Co_{4.8}K_{0.06}Si_{1.6}$$

When the finished catalyst was analyzed by X-ray diffraction, the peaks of bismuth tungstate described above were observed, but no peak was observed which may be ascribed to compounds formed by the combination of bismuth with elements other than oxygen, for example bismuth molybdates.

A portion (1520 ml) of the resulting catalyst was filled in a steel reaction tube having an inside diameter of 25.4 mm to a layer length of 3000 mm, and an external heat medium (molten salt) was heated to 295° C. A starting gas composed of 7% by volume of propylene, 12.6% by volume of oxygen, 10.0% by volume of steam and 70.4% by volume of nitrogen was introduced into the reaction tube, and reacted for a contact time of 2.0 seconds (at NTP). The results shown in Table 1 were obtained.

The reaction products were analyzed by gas chromatography and an acid titration method.

After the catalyst was used for a period of 5000 hours, it was withdrawn and analyzed by X-ray. No appreciable change from the catalyst before use was observed.

COMPARATIVE EXAMPLE 1

A catalyst having the following composition was prepared by the same procedure as in Example 1 except that the calcined product of a bismuth compound and a tungsten compound was not used.

$$Fe_{0.35}Mo_{12}Co_{4.8}K_{0.06}Si_{1.6}$$

The resulting catalyst was used in the same reaction under the same conditions as in Example 1. The results shown in Table 1 were obtained.

COMPARATIVE EXAMPLE 2

A catalyst having the following composition was prepared in the same way as in Example 1 except that tungsten trioxide was not used.

$$Bi_{1.2}Fe_{0.35}Mo_{12}Co_{4.8}K_{0.06}Si_{1.2}$$

The resulting catalyst was used in the same reaction under the same conditions as in Example 1. The results shown in Table 1 were obtained.

COMPARATIVE EXAMPLE 3

A catalyst having the same composition as in Example 1 was obtained by repeating Example 1 except that in Example 1, the bismuth compound and the tungsten compound were calcined at 500° C. for 2 hours. The results shown in Table 1 were obtained.

EXAMPLE 2

Bismuth nitrate (405 g) was dissolved in 920 ml of distilled water acidified with 80 ml of concentrated nitric acid. Sodium tungstate (138 g) was dissolved in 1700 ml of water, and the pH of the solution was adjusted to 2.2 with nitric acid. The solution was then heated to 80° C. and added to the bismuth nitrate solution with stirring. The resulting white precipitate was separated by filtration, and washed with water until a sodium ion was no longer detected. The resulting white cake was treated in the same way as in Example 1 to obtain a yellow powder. When this powder was analyzed by X-ray diffraction (cathode Cu-K$_\alpha$), strong diffraction peaks were observed at d=3.147, 2.719, 1.925 and 1.617. These peaks agree with those of Bi$_2$WO$_6$ shown in the above-cited literature reference. No peak ascribed to bismuth oxide was observed.

Separately, an aqueous solution of 970 g of cobalt nitrate in 800 ml of distilled water, an aqueous solution of 336 g of ferric nitrate in 1000 ml of distilled water, and an aqueous solution of 400 g of silica sol containing 20% by weight of silica and 5.1 g of potassium nitrate in 100 ml of distilled water were added to an aqueous solution of 1766 g of ammonium molybdate in 8000 ml of distilled water, and they were stirred at room temperature.

To the resulting suspension were added 90 ml of concentrated nitric acid and 600 g of ammonium nitrate, and then the above yellow powder was added. The mixture was concentrated with stirring under heat. The concentrated product was then molded and dried in the same way as in Example 1 and then calcined at 450° C. for 6 hours under an air current to form a catalyst having the following composition.

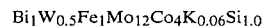

$Bi_1W_{0.5}Fe_1Mo_{12}Co_4K_{0.06}Si_{1.0}$

The resulting catalyst was used in the same reaction under the same conditions as in Example 1, and the results shown in Table 1 were obtained.

EXAMPLE 3

Using the catalyst of Example 1, propylene in a high concentration was reacted with air and steam. The results shown in Table 1 were obtained.

EXAMPLES 4 TO 11

Catalysts having the compositions shown in Table 1 were prepared in the same way as in Example 1. Propylene was oxidized under the conditions shown in Table 1, and the results are also shown in Table 1.

As sources of nickel, cesium, barium, strontium, calcium, aluminum, magnesium and lead, nitrates of these metals were used. As a source of rubidium, rubidium hydroxide was used. As sources of titanium, niobium, antimony and zirconium, oxides of these metals were used. Phosphoric acid was used as a source of phosphorus, and boric acid, as a source of boron.

EXAMPLE 12

A catalyst having the same composition as in Example 1 and prepared by the same method as in Example 1 was molded into the shape of a ring having an outside diameter of 6.0 mm, a length of 6.6 mm and an inside diameter of 1.0 mm. The catalyst was used in the same reaction as in Example 1, and the results obtained are shown in Table 1.

TABLE 1

| | | Example 1 | Example 2 | Example 3 | Example 4 | Example 5 | Example 6 | Example 7 | Example 8 |
|---|---|---|---|---|---|---|---|---|---|
| Composition of the catalyst (atomic ratio) | Bi | 1.2 | 1 | 1.2 | 1.2 | 1.2 | 1.2 | 1.2 | 1.2 |
| | W | 2.4 | 0.5 | 2.4 | 2.4 | 2.4 | 2.4 | 2.4 | 2.4 |
| | Fe | 0.35 | 1 | 0.35 | 1.8 | 1.2 | 1.2 | 1.2 | 2.4 |
| | Mo | 12 | 12 | 12 | 12 | 12 | 12 | 12 | 12 |
| | A | Co 4.8 | Co 4.0 | Co 4.8 | Co 4.8 | Co 4.8 | Co 4.8 | Co 4.8 | Ni 1.0 |
| | B | K 0.06 | K 0.06 | K 0.06 | K 0.05 Ba 0.06 | Cs 0.02 | Sr 0.06 | Ca 0.06 | Rb 0.12 |
| | C | — | — | — | — | — | — | — | P 1.2 |
| | D | Si 1.6 | Si 1.6 | Si 1.6 | Si 1.6 | Si 1.6 Ti 1.2 | Si 1.6 | Si 1.6 | Si 5.0 |
| Composition of the starting gas (vol. %) | Propylene | 7 | 7 | 9 | 7 | 7 | 7 | 7 | 7 |
| | Oxygen | 12.6 | 12.6 | 13.5 | 12.6 | 12.6 | 12.6 | 12.6 | 12.6 |
| | Steam | 10 | 10 | 26.7 | 10 | 10 | 10 | 0 | 10.0 |
| | Nitrogen and others | 70.4 | 70.4 | 50.8 | 70.4 | 70.4 | 70.4 | 80.4 | 70.4 |
| Reaction temperature (°C.) | | 295 | 295 | 280 | 300 | 310 | 300 | 300 | 310 |
| Contact time (seconds) | | 2.0 | 2.0 | 2.0 | 2.0 | 2.0 | 2.0 | 2.0 | 2.0 |
| Conversion of propylene (mole %) | | 97.5 | 97.0 | 96.5 | 97.0 | 93.5 | 95.1 | 96.8 | 95.5 |
| Selectivity of acrolein (mole %) | | 88.4 | 90.2 | 90.4 | 86.1 | 87.6 | 85.1 | 84.6 | 79.1 |
| Selectivity of acrylic acid (mole %) | | 8.3 | 6.8 | 5.8 | 10.3 | 9.7 | 11.5 | 11.8 | 13.0 |
| One-pass yield of acrolein (mole %) | | 86.2 | 87.5 | 87.2 | 83.5 | 81.9 | 80.9 | 81.9 | 75.5 |
| One-pass yield of acrylic acid (mole %) | | 8.1 | 6.6 | 5.7 | 10.0 | 9.1 | 10.9 | 11.4 | 12.4 |
| Total yield of acrolein and acrylic acid (mole %) | | 94.3 | 94.1 | 92.9 | 93.5 | 91.0 | 91.8 | 93.3 | 87.9 |

| | | Example 9 | Example 10 | Example 11 | Example 12 | Comparative Example 1 | Comparative Example 2 | Comparative Example 3 |
|---|---|---|---|---|---|---|---|---|
| Composition of the catalyst (atomic ratio) | Bi | 1.2 | 1.2 | 1.2 | 1.2 | — | 1.2 | 1.2 |
| | W | 2.4 | 2.4 | 2.4 | 2.4 | — | — | 2.4 |
| | Fe | 2.4 | 3.0 | 3.0 | 0.35 | 0.35 | 0.35 | 0.35 |
| | Mo | 12 | 12 | 12 | 12 | 12 | 12 | 12 |
| | A | Ni 1.0 | Co 0.6 | Ni 8.0 | Co 4.8 | Co 4.8 | Co 4.8 | Co 4.8 |

TABLE 1-continued

|   |   |   |   |   |   |   |   |   |   |   |   |   |   |   |   |   |
|---|---|---|---|---|---|---|---|---|---|---|---|---|---|---|---|---|
|   |   |   | Co | 3.0 |   |   |   |   |   |   |   |   |   |   |   |   |
|   | B |   | K | 0.25 | K | 0.05 | Cs | 0.03 | K | 0.06 | K | 0.06 | K | 0.06 | K | 0.06 |
|   |   |   |   |   | Ca | 0.05 | Mg | 0.05 |   |   |   |   |   |   |   |   |
|   | C |   | B | 2.8 | Pb | 1.0 | Nb | 1.0 | — | — | — | — | — | — | — | — |
|   |   |   |   |   |   |   | Sb | 1.0 |   |   |   |   |   |   |   |   |
|   | D |   | Si | 5.0 | Zr | 1.0 | Si | 1.6 | Si | 1.60 | Si | 1.6 | Si | 1.6 | Si | 1.6 |
|   |   |   | Al | 1.0 |   |   |   |   |   |   |   |   |   |   |   |   |
| Composition of | Propylene |   | 7 |   | 7 |   | 7 |   | 7 |   | 7 |   | 7 |   | 7 |   |
| the starting gas | Oxygen |   | 12.6 |   | 12.6 |   | 12.6 |   | 12.6 |   | 12.6 |   | 12.6 |   | 12.6 |   |
| (vol. %) | Steam |   | 10.0 |   | 10.0 |   | 10.0 |   | 10.0 |   | 10.0 |   | 10.0 |   | 10.0 |   |
|   | Nitrogen and others |   | 70.4 |   | 70.4 |   | 70.4 |   | 70.4 |   | 70.4 |   | 70.4 |   | 70.4 |   |
| Reaction temperature (°C.) |   |   | 310 |   | 320 |   | 290 |   | 295 |   | 400 |   | 95 |   | 295 |   |
| Contact time (seconds) |   |   | 2.0 |   | 2.0 |   | 2.0 |   | 2.0 |   | 2.0 |   | 2.0 |   | 2.0 |   |
| Conversion of propylene (mole %) |   |   | 94.3 |   | 92.9 |   | 93.6 |   | 98.5 |   | 9.5 |   | 85.8 |   | 89.4 |   |
| Selectivity of acrolein (mole %) |   |   | 77.5 |   | 77.0 |   | 75.0 |   | 90.5 |   | 75.0 |   | 85.5 |   | 87.5 |   |
| Selectivity of acrylic acid (mole %) |   |   | 12.7 |   | 12.1 |   | 12.9 |   | 7.0 |   | 3.6 |   | 6.5 |   | 9.5 |   |
| One-pass yield of acrolein (mole %) |   |   | 73.1 |   | 71.5 |   | 70.2 |   | 89.1 |   | 7.1 |   | 73.4 |   | 78.2 |   |
| One-pass yield of acrylic acid (mole %) |   |   | 12.0 |   | 11.2 |   | 12.1 |   | 6.9 |   | 0.3 |   | 5.6 |   | 8.5 |   |
| Total yield of acrolein and acrylic acid (mole %) |   |   | 85.1 |   | 82.7 |   | 82.3 |   | 96.0 |   | 7.4 |   | 79.0 |   | 86.7 |   |

EXAMPLE 13

A catalyst having the following composition was prepared in the same way as in Example 1 except that the temperature for calcining the catalyst was changed to 500° C.

The catalyst was filled in a steel reaction tube having an inside diameter of 25.4 mm to a layer length of 3,000 mm, and of an external heat medium was heated to 340° C. A starting gas composed of 6% by volume of isobutylene, 13.2% by volume of oxygen, 10.0% by volume of steam and 70.8% by volume of nitrogen was introduced into the reaction tube and reacted for a contact time of 2.5 seconds. The results are shown in Table 2.

The product was analyzed by gas chromatography.

After the catalyst was used in the reaction for a period of 5,000 hours, it was withdrawn and analyzed by X-ray. No appreciable change from the catalyst before use was noted.

COMPARATIVE EXAMPLE 4

A catalyst having the following composition was prepared in the same way as in Example 13 except that the high-temperature calcined product of the bismuth compound and the tungsten compound was not used.

$Fe_{0.35}Mo_{12}Co_{6.0}K_{0.5}Si_{1.0}$

The resulting catalyst was used in the same reaction under the same conditions as in Example 13, and the results shown in Table 2 were obtained.

COMPARATIVE EXAMPLE 5

A catalyst having the following composition was prepared in the same way as in Example 13 except that tungsten trioxide was not used.

$Bi_{1.2}Fe_{0.35}Mo_{12}Co_{6.0}K_{0.5}Si_{1.0}$

The resulting catalyst was used in the same reaction under the same reaction conditions as in Example 13, and the results shown in Table 2 were obtained.

COMPARATIVE EXAMPLE 6

A catalyst having the same composition as in Example 13 was obtained in the same way as in Example 13 except that the bismuth compound and the tungsten compound were treated at 500° C. for 2 hours. The resulting catalyst was used in the same reaction under the same conditions as in Example 13, and the results shown in Table 2 were obtained.

EXAMPLE 14

A catalyst having the following composition was prepared in the same way as in Example 2 except that rubidium hydroxide was used instead of potassium nitrate, and the catalyst calcining temperature was changed to 500° C.

$Bi_{3.6}W_{1.8}Fe_{1.2}Mo_{12}Co_6Rb_{0.5}Si_{1.0}$

The resulting catalyst was used in the same reaction and under the same conditions as in Example 13, and the results shown in Table 2 were obtained.

EXAMPLE 15

Bismuth nitrate (485 g) was dissolved in 100 ml of distilled water acidified with 104 ml of concentrated nitric acid. To the aqueous solution was added 1100 ml of aqueous ammonia (28%) to obtain a white precipitate. The precipitate was separated by filtration, and washed with water. The resulting white cake was fully mixed with 279 g of tungsten trioxide. The mixture wa dried at 230° C. for 16 hours, and calcined at 750° C. for 2 hours under an air current. The resulting yellow mass was pulverized to a size smaller than 100 mesh to obtain a yellow powder.

Separately, an aqeuous solution of 873 g of cobalt nitrate in 800 ml of distilled water, an aqueous solution of 323 g of ferric nitrate in 1000 ml of distilled water, and an aqueous solution of 150 g of silica sol containing 20% by weight of silica and 48.7 g of cesium nitrate in 300 ml of distilled water were added to an aqueous solution of 1060 g of ammonium molybdate in 8000 ml of distilled water, and the mixture was stirred at room temperature.

Concentrated nitric acid (90 ml) and 500 g of ammonium nitrate were added to the resulting suspension, and then the above yellow powder was added. The mixture was concentrated with stirring under heat, molded in the same way as in Example 13, and then calcined at 500° C. for 6 hours under an air current to give a catalyst having the following composition.

$Bi_{2.0}W_{2.4}Fe_{1.6}Mo_{12}Co_6Si_{1.0}Cs_{0.5}$

The resulting catalyst was used in the same reaction under the same conditions as in Example 13, and the results shown in Table 2 were obtained.

EXAMPLES 16 TO 22

Catalysts having the compositions shown in Table 2 were prepared in the same way as in Example 13. iso-Butylene was oxidized under the reaction conditions shown in Table 2, and the results shown in Table 2 were obtained.

As sources of thallium and cerium, their nitrates were used. Tin chloride was used as a source of tin, and ortho-arsenic acid, as a source of arsenic.

EXAMPLE 23

A catalyst having the same composition as in Example 13 and prepared by the same method as in Example 13 was molded into the shape of a ring having an outside diameter of 6.0 mm, a length of 6.6 mm and an inside diameter of 2.0 mm. The ring-like catalyst was used in the same reaction as in Example 13, and the results shown in Table 2 were obtained.

Selectivity of isobutylene: 1.5%
Selectivity of methacrolein: 85.2%
Selectivity of methacrylic acid: 2.6%
One-pass yield of isobutylene: 1.5%
One-pass yield of methacrolein: 85.2%
One-pass yield of methacrylic acid: 2.6%

What is claimed is:

1. A catalyst for the production of unsaturated aldehydes, said catalyst being represented by the general formula $$Bi_aW_bFe_cMo_dA_eB_fC_gD_hO_x$$

wherein Bi represents bismuth, W represents tungsten, Fe represents iron, Mo represents molybdenum, O represents oxygen, A represents nickel (Ni) and/or cobalt (Co), B represents at least one element selected from the group consisting of alkali metals, alkaline earth metals and thallium, C represents at least one element selected from the group consisting of phosphorus (P), arsenic (As), boron (B), antimony (Sb), tin (Sn), cerium (Ce), lead (Pb)

TABLE 2

| | | Example | | | | | | | | | | |
|---|---|---|---|---|---|---|---|---|---|---|---|---|
| | | 13 | 14 | 15 | 16 | 17 | 18 | 19 | 20 | 21 | 22 | 23 |
| Composition of the | Bi | 1.2 | 3.6 | 2.0 | 1.2 | 1.2 | 1.2 | 1.2 | 1.2 | 1.2 | 1.2 | 1.2 |
| catalyst (atomic ratio) | W | 2.4 | 1.8 | 2.4 | 2.4 | 2.4 | 2.4 | 2.4 | 2.4 | 2.4 | 2.4 | 2.4 |
| | Fe | 0.35 | 1.2 | 1.6 | 0.35 | 0.35 | 0.35 | 3.0 | 3.0 | 2.4 | 2.4 | 0.35 |
| | Mo | 12 | 12 | 12 | 12 | 12 | 12 | 12 | 12 | 12 | 12 | 12 |
| | A | Co 6.0 | Co 6.0 | Co 6.0 | Co 6.0 Ni 3.0 | Co 6.0 | Co 6.0 | Co 6.0 | Ni 8.0 | Co 3.0 Ni 1.0 | Co 3.0 Ni 1.0 | Co 6.0 |
| | B | K 0.5 | Rb 0.5 | Cs 0.5 | Cs 0.5 Ba 0.1 | Tl 0.5 | K 0.5 Sr 0.2 | K 0.5 Ca 0.2 | Cs 0.2 Mg 0.2 | K 1.0 | K 1.0 | K 0.5 |
| | C | — | — | — | — | P 0.5 | Ce 1.0 | Pb 1.0 | Nb 1.0 Sb 1.0 | B 2.8 | As 0.5 Sn 0.5 | — |
| | D | Si 1.0 | Si 1.0 | Si 1.0 | Si 5.0 | Si 1.0 Al 1.0 | Si 1.0 Ti 1.0 | Si 1.0 | Si 1.0 | Si 5.0 Al 1.0 | Zr 1.0 | Si 1.0 |
| Reaction temperature (°C.) | | 320 | 330 | 330 | 320 | 320 | 320 | 320 | 315 | 330 | 320 | 320 |
| Contact time (seconds) | | 2.5 | 2.5 | 2.5 | 2.5 | 2.5 | 2.5 | 2.5 | 2.5 | 2.5 | 2.5 | 2.5 |
| Conversion of isobutylene (mole %) | | 99.5 | 98.7 | 99.0 | 99.1 | 98.9 | 98.8 | 98.3 | 99.3 | 97.3 | 97.4 | 99.5 |
| Selectivity (mole %) | Methacrolein | 85.2 | 86.4 | 86.9 | 85.1 | 81.0 | 77.9 | 77.6 | 76.5 | 74.8 | 74.2 | 86.6 |
| | Methacrylic acid | 2.9 | 2.4 | 2.2 | 2.7 | 3.0 | 4.0 | 4.4 | 4.1 | 4.8 | 5.0 | 2.3 |
| One-pass yield (mole %) | Methacrolein | 84.8 | 85.3 | 86.0 | 84.3 | 80.1 | 77.0 | 76.3 | 76.0 | 72.8 | 72.3 | 86.2 |
| | Methacrylic acid | 2.9 | 2.4 | 2.2 | 2.7 | 3.0 | 4.0 | 4.3 | 4.1 | 4.7 | 4.9 | 2.3 |

| | | | Comparative Example | | |
|---|---|---|---|---|---|
| | | | 4 | 5 | 6 |
| Composition of the | Bi | | — | 1.2 | 1.2 |
| catalyst (atomic ratio) | W | | — | — | 2.4 |
| | Fe | | 0.35 | 0.35 | 0.35 |
| | Mo | | 12 | 12 | 12 |
| | A | | Co 6.0 | Co 6 | Co 6 |
| | B | | K 0.5 | K 0.5 | K 0.5 |
| | C | | — | — | — |
| | D | | Si 1.0 | Si 1.0 | Si 1.0 |
| Reaction temperature (°C.) | | | 400 | 320 | 320 |
| Contact time (seconds) | | | 2.5 | 2.5 | 2.5 |
| Conversion of isobutylene (mole %) | | | 11.1 | 90.2 | 92.3 |
| Selectivity (mole %) | Methacrolein | | 58.6 | 86.3 | 86.1 |
| | Methacrylic acid | | 18.9 | 4.3 | 3.9 |
| One-pass yield (mole %) | Methacrolein | | 6.5 | 77.8 | 79.5 |
| | Methacrylic acid | | 2.1 | 3.9 | 3.6 |

EXAMPLE 24

Using the catalyst of Example 14, a starting gas composed of 6% by volume of t-butanol, 13.2% by volume of oxygen, 4% by volume of steam and 76.8% by volume of nitrogen was introduced into the same reaction tube as used in Example 14 to oxidize t-butanol for a contact time of 2.5 seconds and at a molten salt temperature of 330° C. The results were as follows:

Conversion of t-butanol: 100% and niobium (Nb), D represents at least one element selected from the group consisting of silicon (Si), aluminum (Al), zirconium (Zr) and titanium (Ti), a, b, c, d, e, f, g, h and x represent the atomic ratios of the individual elements, and when d is taken as 12, $a=0.1-10.0$, $b=0.5-10.0$ (provided that $a/b=0.01-6.0$), $c=0.1-10.0$, $e=2.0-20.0$, $f=0.001-10.0$, $g=0-10.0$, and $h=0-30$, and x takes a number determined by the atomic valences of the individual elements; said catalyst having been calcined in air at a temperature of from 400° C.–600° C.

the Bi component being introduced thereinto in the form of a bismuth tungstate obtained beforehand by calcining a mixture of a bismuth compound and a tungsten compound at a temperature of 600° to 900° C.

2. The catalyst of claim 1 wherein when d is taken as 12, a=0.5–5.0, b=0.5–4.0 (provided that a/b=0.1–4.0), c=0.2–5.0, e=3.0–10.0, f=0.02–2.0, g=0–5.0 and h=0.5–10.0.

* * * * *